US006652547B2

(12) United States Patent
Rabiner et al.

(10) Patent No.: US 6,652,547 B2
(45) Date of Patent: *Nov. 25, 2003

(54) APPARATUS AND METHOD OF REMOVING OCCLUSIONS USING ULTRASONIC MEDICAL DEVICE OPERATING IN A TRANSVERSE MODE

(75) Inventors: Robert Rabiner, North Reading, MA (US); Bradley A. Hare, Chelmsford, MA (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 74 days.

This patent is subject to a terminal disclaimer.

(21) Appl. No.: 09/776,015

(22) Filed: Feb. 2, 2001

(65) Prior Publication Data

US 2002/0077643 A1 Jun. 20, 2002

Related U.S. Application Data

(63) Continuation-in-part of application No. 09/618,352, filed on Jul. 19, 2000
(60) Provisional application No. 60/157,824, filed on Oct. 5, 1999, and provisional application No. 60/178,901, filed on Jan. 28, 2000.

(51) Int. Cl.[7] .............................. A61B 17/22; A61N 7/00
(52) U.S. Cl. ...................... 606/159; 606/169; 606/171; 604/22
(58) Field of Search ................................ 604/22, 95.03, 604/509; 606/159, 169–171, 192; 601/2, 4

(56) References Cited

U.S. PATENT DOCUMENTS

| 3,805,787 A | 4/1974 | Banko ........................ 128/276 |
| 4,504,264 A | 3/1985 | Kelman ....................... 604/22 |
| 4,870,953 A | * 10/1989 | DonMicheal et al. ......... 604/22 |
| 4,922,902 A | 5/1990 | Wuchinich et al. ........... 604/22 |
| 4,931,047 A | 6/1990 | Broadwin et al. ............ 604/22 |

(List continued on next page.)

FOREIGN PATENT DOCUMENTS

GB          2325192 A   * 11/1998 ............ A23G/3/02

OTHER PUBLICATIONS

PCT International Search Report for International Application No. PCT/US02/02059 dated Jul. 9, 2002.

Primary Examiner—John J. Calvert
Assistant Examiner—Shuan R Hurley
(74) Attorney, Agent, or Firm—Palmer & Dodge, LLP; Richard B. Smith; David J. Dykeman

(57) ABSTRACT

A method for removing an occlusion is provided comprising introducing a transverse mode ultrasonic probe into a blood vessel, positioning the probe in proximity to the occlusion, and transmitting ultrasonic energy to the probe, until the occlusion is removed. The probe has a small cross-sectional lumen and is articulable for navigating in a tortuous vessel path. The probe can be used with acoustic and/or aspirations sheaths to enhance destruction and removal of an occlusion. The probe can also be used with a balloon catheter. The probe, sheaths, and catheter can be provided in a sharps container which further provides a means of affixing and detaching the probe from an ultrasonic medical device.

37 Claims, 10 Drawing Sheets

U.S. PATENT DOCUMENTS

| | | | | |
|---|---|---|---|---|
| 4,961,424 A | | 10/1990 | Kubota et al. | 128/24 A |
| 4,989,583 A | | 2/1991 | Hood | 128/24 A |
| 5,015,227 A | | 5/1991 | Broadwin et al. | 604/22 |
| 5,112,300 A | | 5/1992 | Ureche | 604/22 |
| 5,139,496 A | * | 8/1992 | Hed | 606/23 |
| 5,163,421 A | | 11/1992 | Bernstein et al. | 128/24.1 |
| 5,180,363 A | | 1/1993 | Idemoto et al. | 202/32 |
| 5,255,669 A | * | 10/1993 | Kubota et al. | 601/3 |
| 5,269,297 A | | 12/1993 | Weng et al. | 128/24 AA |
| 5,324,255 A | * | 6/1994 | Passafaro et al. | 604/22 |
| 5,391,144 A | * | 2/1995 | Sakurai et al. | 604/22 |
| 5,725,494 A | | 3/1998 | Brisken | 604/22 |
| 5,728,062 A | | 3/1998 | Brisken | 604/22 |
| 5,735,811 A | | 4/1998 | Brisken | 604/22 |
| 5,836,897 A | * | 11/1998 | Sakurai et al. | 601/2 |
| 5,916,192 A | * | 6/1999 | Nita et al. | 604/22 |
| 5,928,218 A | | 7/1999 | Gelbfish | 604/540 |
| 5,931,805 A | | 8/1999 | Brisken | 604/22 |
| 5,957,882 A | * | 9/1999 | Nita et al. | 604/22 |
| 6,287,271 B1 | * | 9/2001 | Dubrul et al. | 604/22 |
| 6,287,272 B1 | * | 9/2001 | Brisken et al. | 604/22 |
| 2002/0029054 A1 | * | 3/2002 | Rabiner et al. | 606/169 |
| 2002/0055754 A1 | * | 5/2002 | Ranucci et al. | 606/169 |
| 2002/0077550 A1 | * | 6/2002 | Rabiner et al. | 600/439 |
| 2002/0107446 A1 | * | 8/2002 | Rabiner et al. | 600/439 |

\* cited by examiner

APPARATUS AND METHOD OF REMOVING OCCLUSIONS USING ULTRASONIC MEDICAL DEVICE OPERATING IN A TRANSVERSE MODE

This is a continuation-in-part of Provisional Application Nos. 60/157,824, filed Oct. 5, 1999; 60/178,901, filed Jan. 28, 2000 and application Ser. No. 09/618,352, filed Jul. 19, 2000.

FIELD OF THE INVENTION

The present invention relates generally to medical devices, and more particularly to an apparatus and method for using an ultrasonic medical device operating in a transverse mode to remove occlusions from a blood vessel. The invention also relates to an apparatus and method of using balloon catheters emitting ultrasonic energy in transverse mode, to remove vascular occlusions.

BACKGROUND OF THE INVENTION

Vascular occlusions (clots or thrombi and occlusional deposits, such as calcium, fatty deposits, or plaque), result in the restriction or blockage of blood flow in the vessels in which they occur. Occlusions result in oxygen deprivation ("ischemia") of tissues supplied by these blood vessels. Prolonged ischemia results in permanent damage of tissues which can lead to myocardial infarction, stroke, or death. Targets for occlusion include coronary arteries, peripheral arteries and other blood vessels. The disruption of an occlusion or thrombolysis can be effected by pharmacological agents and/or or mechanical means. However, many thrombolytic drugs are associated with side effects such as severe bleeding which can result in cerebral hemorrhage. Mechanical methods of thrombolysis include balloon angioplasty, which can result in ruptures in a blood vessel, and is generally limited to larger blood vessels. Scarring of vessels is common, which may lead to the formation of a secondary occlusion (a process known as restenosis). Another common problem is secondary vasoconstriction (classic recoil), a process by which spasms or abrupt closure of the vessel occurs. These problems are common in treatments employing interventional devices. In traditional angioplasty, for instance, a balloon catheter is inserted into the occlusion, and through the application of hydraulic forces in the range of ten to fourteen atmospheres of pressure, the balloon is inflated. The non-compressible balloon applies this significant force to compress and flatten the occlusion, thereby opening the vessel for blood flow. However, these extreme forces result in the application of extreme stresses to the vessel, potentially rupturing the vessel, or weaking it thereby increasing the chance of post-operative aneurysm, or creating vasoconstrictive or restenotic conditions. In addition, the particulate matter isn't removed, rather it is just compressed. Other mechanical devices that drill through and attempt to remove an occlusion have also been used, and create the same danger of physical damage to blood vessels.

Ultrasonic probes are devices which use ultrasonic energy to fragment body tissue (see, e.g., U.S. Pat. No. 5,112,300; U.S. Pat. No. 5,180,363; U.S. Pat. No. 4,989,583; U.S. Pat. No. 4,931,047; U.S. Pat. No. 4,922,902; and U.S. Pat. No. 3,805,787) and have been used in many surgical procedures. The use of ultrasonic energy has been proposed both to mechanically disrupt clots, and to enhance the intravascular delivery of drugs to clot formations (see, e.g., U.S. Pat. No. 5,725,494; U.S. Pat. No. 5,728,062; and U.S. Pat. No. 5,735,811). Ultrasonic devices used for vascular treatments typically comprise an extracorporeal transducer coupled to a solid metal wire which is then threaded through the blood vessel and placed in contact with the occlusion (see, e.g., U.S. Pat. No. 5,269,297). In some cases, the transducer is delivered to the site of the clot, the transducer comprising a bendable plate (see, U.S. Pat. No. 5,931,805).

The ultrasonic energy produced by an ultrasonic probe is in the form of very intense, high frequency sound vibrations which result in powerful chemical and physical reactions in the water molecules within a body tissue or surrounding fluids in proximity to the probe. These reactions ultimately result in a process called "cavitation," which can be thought of as a form of cold (i.e., non-thermal) boiling of the water in the body tissue, such that microscopic bubbles are rapidly created and destroyed in the water creating cavities in their wake. As surrounding water molecules rush in to fill the cavity created by collapsed bubbles, they collide with each other with great force. This process is called cavitation and results in shock waves running outward from the collapsed bubbles which can wear away or destroy material such as surrounding tissue in the vicinity of the probe.

Some ultrasonic probes include a mechanism for irrigating an area where the ultrasonic treatment is being performed (e.g., a body cavity or lumen) to wash tissue debris from the area. Mechanisms used for irrigation or aspiration described in the art are generally structured such that they increase the overall cross-sectional profile of the probe, by including inner and outer concentric lumens within the probe to provide irrigation and aspiration channels. In addition to making the probe more invasive, prior art probes also maintain a strict orientation of the aspiration and the irrigation mechanism, such that the inner and outer lumens for irrigation and aspiration remain in a fixed position relative to one another, which is generally closely adjacent the area of treatment. Thus, the irrigation lumen does not extend beyond the suction lumen (i.e., there is no movement of the lumens relative to one another) and any aspiration is limited to picking up fluid and/or tissue remnants within the defined distance between the two lumens.

Another drawback of existing ultrasonic medical probes is that they typically remove tissue slowly in comparison to instruments which excise tissue by mechanical cutting. Part of the reason for this is that most existing ultrasonic devices rely on a longitudinal vibration of the tip of the probe for their tissue-disrupting effects. Because the tip of the probe is vibrated in a direction in line with the longitudinal axis of the probe, a tissue-destroying effect is only generated at the tip of the probe. One solution that has been proposed is to vibrate the tip of the probe in a transverse direction—i.e. perpendicular to the longitudinal axis of the probe,—in addition to vibrating the tip in the longitudinal direction. For example, U.S. Pat. No. 4,961,424 to Kubota, et al. discloses an ultrasonic treatment device which produces both a longitudinal and transverse motion at the tip of the probe. The Kubota, et al. device, however, still relies solely on the tip of the probe to act as a working surface. Thus, while destruction of tissue in proximity to the tip of the probe is more efficient, tissue destruction is still predominantly limited to the area in the immediate vicinity at the tip of the probe. U.S. Pat. No. 4,504,264 to Kelman discloses an ultrasonic treatment device which improves the speed of ultrasonic tissue removal by oscillating the tip of the probe in addition to relying on longitudinal vibrations. Although tissue destruction at the tip of the device is more efficient, the tissue destroying effect of the probe is still limited to the tip of the probe.

There is a need in the art for improved devices, systems, and methods, for treating vascular diseases, particularly stenotic diseases which occlude the coronary and other arteries. In particular, there is a need for methods and devices for enhancing the performance of angioplasty procedures, where the ability to introduce an angioplasty catheter through a wholly or partly obstructed blood vessel lumen can be improved. There is also a need for mechanisms and methods that decrease the likelihood of subsequent clot formation and restenosis.

SUMMARY OF THE INVENTION

The invention is directed to a method and an apparatus for removing occlusions in a blood vessel. The invention has particular application in removal of occlusions in saphenous vein grafts used in coronary bypass procedures, restoring these grafts to patency without damaging anastomosing blood vessels. The method according to the invention comprises inserting a probe member comprising a longitudinal axis into a vessel, positioning the member in proximity to the occlusion, and providing ultrasonic energy to the member. The device is designed to have a small cross-sectional profile, which also allows the probe to flex along its length, thereby allowing it to be used in a minimally-invasive manner. The probe, because it vibrates transversely, generates a plurality of cavitation nodes along the longitudinal axis of the member, thereby efficiently destroying the occlusion. A significant feature of the invention is the retrograde movement of debris, e.g., away from the tip of the probe, resulting from the transversely generated energy. Probes of the present invention are described in the Applicant's co-pending provisional applications U.S. Ser. Nos. 60/178, 901 and 60/225,060 which further describe the design parameters for an ultrasonic probe operating in a transverse mode and the use of such a probe to remodel tissues. The entirety of these applications are herein incorporated by reference.

In one aspect, the invention relates to one or more sheaths which can be adapted to the probe tip, thereby providing a means of containing, focussing, and transmitting energy generated along the length of the probe to one or more defined locations. Sheaths for use with an ultrasonic medical device are described in the Applicant's co-pending utility application U.S. Ser. No. 09/618,352, the entirety of which is hereby incorporated by reference. The sheaths of the present invention also provide the user with a means of protecting regions of tissue from physical contact with the probe tip. In one embodiment of the invention the sheaths also comprise a means for aspiration and irrigation of the region of probe activity. In another embodiment of the invention, a plurality of sheaths are used in combination to provide another level of precision control over the direction of cavitation energy to a tissue in the vicinity of the probe. In one embodiment of the invention, the sheath encloses a means of introducing fluid into the site of the procedure, and a means for aspirating fluid and tissue debris from the site of the procedure. In a further embodiment, the probe tip can be moved within the sheath. In yet another embodiment, the irrigation and aspiration means, and the probe tip, can all be manipulated and repositioned relative to one another within the sheath. In another embodiment, the sheath is shaped in such a way that it may capture or grasp sections of tissue which can be ablated with the probe. In yet another embodiment, the sheath provides a guide for the probe tip, protecting tissues from accidental puncture by the sharp, narrow diameter tip, or from destruction by energy emitted radially from the probe during introduction of the probe to the site. The sheath may be applied to the probe tip prior to insertion of the probe into the patient, or the sheath can be inserted into the patient prior to the insertion of the probe. The sheath of the present invention can be used to fix the location of one or more shapes relative to the nodes or anti-nodes of a probe acting in transverse action. The location of the reflective shapes can amplify the acoustical wave thereby magnifying the energy. This allows for the use of very small diameter probes which themselves would not have the requisite structural integrity to apply and translate acoustical energy into sufficient mechanical energy to enable ablation of tissues. The reflective shapes can also focus or redirect the energy, effectively converting a transverse probe emitting cavitation energy along its length, to a directed, side fire ultrasonic device.

In another embodiment, the probe, which may or may not contain a probe sheath, is used in conjunction with an expandable balloon dilatation catheter, providing a means of resolving the occlusion without imparting stress, or inflicting stress injury to a vessel. The balloon catheter acts as a carrier means for guiding the probe wire to the desired site, and acts as a means to position the wire within the lumen of the vessel. With the balloon inserted within the confines of an occlusion, inflation of the balloon provides a means of continuous contact with the potentially irregularly shaped vessel lumen. Introduction of ultrasonic energy into the balloon by the transversely vibrating probe wire thereby results in uniform communication of energy to the regions of the occluded vessel in contact with the balloon. Since the balloon is inflated to much lower pressures than in traditional balloon angioplasty procedures, neither the occlusion or the vessel is compressed, thereby eliminating the problems of stress injury to the vessel. Likewise, as the ultrasound energy fragments the occlusion, the vessel is cleared of the problematic material, rather than simply compressing it into the vessel.

In one embodiment of the invention, a light transmitting element in inserted into the blood vessel along with, or after, the probe (with or without probe sheath) and balloon catheter. The light transmitting element is transmits optical data about the occlusion. In another embodiment of the invention, the probe/sheath and balloon catheter is used with such medical devices, such as a stent, stent graft, trocar, or other such intravascular devices. The invention is particularly useful in clearing occlusions within stents or other such devices where compression is undesirable or not warranted.

In another aspect of the invention, the probe, with or without a probe sheath, and with or without the balloon catheter, may be provided in a sharps container, in the form of a kit. A sharps container of the present invention is the subject of the Applicant's co-pending utility application U.S. Ser. No. 09/775,908, the entirety of which is hereby incorporated by reference. In yet another embodiment, the kit provides instructions, for example, instructions for assembling and tuning the probe, and the appropriate frequency range for the medical procedure. The kit may further comprise packaging whereby the probe, sheath, and balloon catheter are pre-sterilized, and sealed against environmental contaminants. In another embodiment, the container complies with regulations governing the storage, handling, and disposal of sharp medical devices, and used medical devices such as a sheath or balloon catheter.

DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

In one embodiment, as shown in FIG. 1, the transverse mode ultrasonic medical device 1 comprises an elongated probe 6 which is coupled to a device providing a source or generation means for the production of ultrasonic energy (shown in phantom in the Figure as 66). The probe 6 transmits ultrasonic energy received from the generator along its length. The probe is capable of engaging the ultrasonic generator at one terminus with sufficient restraint to form an acoustical mass, that can propagate the ultrasonic energy provided by the generator. The other terminus of the probe comprises a tip 22, which has a small diameter enabling the tip to flex along its longitude. In one embodiment of the invention, the probe diameter decreases at defined intervals 14, 18, 20, and 22. Energy from the generator is transmitted along the length of the probe, causing the probe to vibrate. In this embodiment, one of the probe intervals 18 has at least one groove 45.

FIG. 3a shows a transverse mode probe according to one embodiment of the invention comprising the semi-cylindrical sheath 107 and a second sheath 108. In this embodiment, the second sheath is cylindrical, and is capable of containing the first sheath 107, as well as the probe 6.

FIG. 3b shows another embodiment of the invention wherein the sheath 121 comprises a cylindrical structure of a sufficient diameter to contain the probe 6, visible for the purpose of illustration. The sheath 121 comprises at least one fenestration 111, which allows the cavitation energy emitted from the probe tip to be communicated to an area outside the sheath, otherwise the energy is contained by the sheath.

FIG. 3c shows an embodiment of the present invention wherein the hollow cylindrical sheath 121 has a plurality of arcutate fenestrations 111.

FIG. 3d shows an embodiment of the present invention wherein the probe 6 is contained within a sheath 121 which comprises a plurality of arcutate fenestrations 111, and at least one acoustic reflective element 122, which is adapted to the interior surface of the sheath.

FIG. 3e shows an embodiment of the present invention comprising a sheath 121 further comprising two semi-cylindrical halves 109, each half connected to the other by one or more connecting means 113. The probe 6 is capable of being substantially contained within the sheath. The cavitation energy generated by the probe tip 22 is contained by the semi-cylindrical halves 109, where they occlude the probe tip.

FIG. 3f shows an embodiment of the present invention wherein the sheath further comprises at least two cylinders 104, each cylinder connected to the other by at least one connecting means 113. The probe 6 is capable of being substantially contained within the sheath. The cavitation energy generated by the probe tip 22 is contained by the cylinders 104, where they occlude the probe tip.

FIG. 7 shows the ultrasonic medical device comprising an ultrasonic probe for removal of an occlusion "O" from a blood vessel "By".

FIG. 8 shows the ultrasonic medical device comprising an ultrasonic probe and a sheath assembly for selectively ablating an occlusion "O" from a blood vessel "BV".

FIG. 9 shows the ultrasonic medical device used in conjunction with a balloon catheter for removal of an occlusion "O" from a blood vessel "BV".

FIG. 10 shows the ultrasonic medical device used in conjunction with a series of sheaths and a balloon catheter 91.

DETAILED DESCRIPTION

Figure 1:
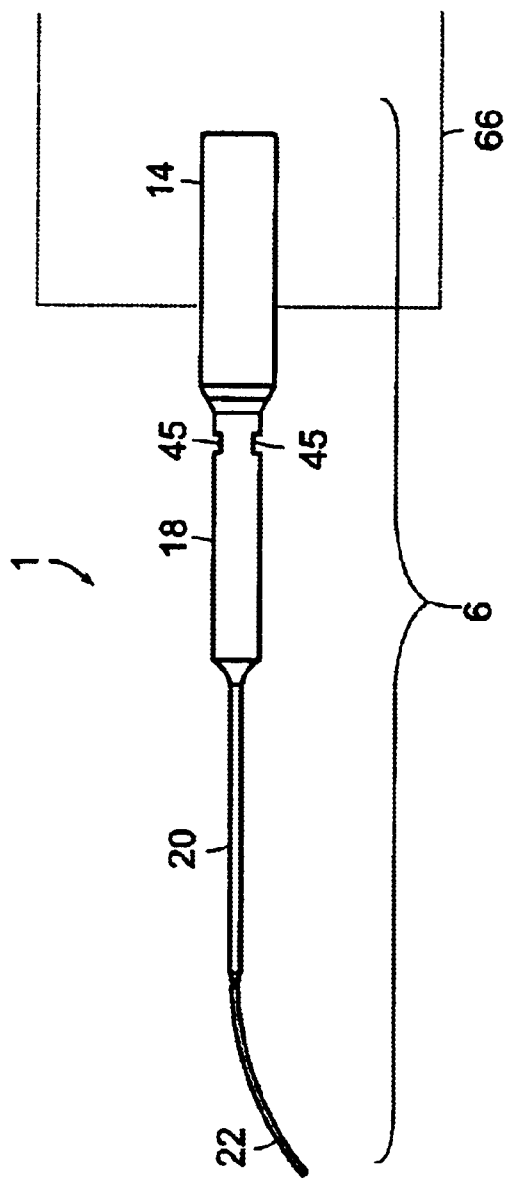
Figure 2:
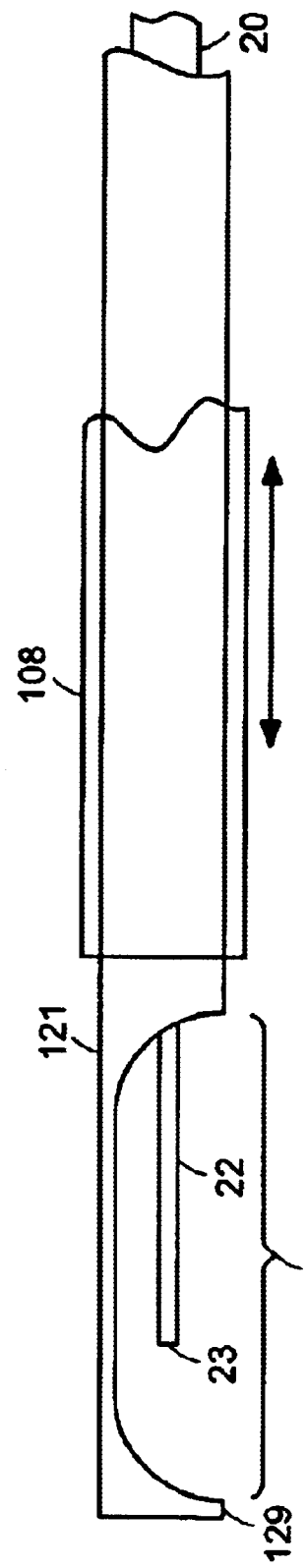
FIG. 2 shows an embodiment of the invention wherein the probe 6 is substantially contained within a cylindrical sheath 121 capable of modulating the energy omitted by an active probe, and shielding tissues from puncture from a sharp probe tip. The sheath 121 shown in this illustration has been modified such that one of the terminal ends of the sheath is substantially open, defining a fenestration or aperture 111, which exposes the probe tip 22 and 23. The terminus of the sheath 129 is shaped to provide a means for manipulating tissue to bring it into proximity with the probe 22 and 23. Also shown in this embodiment is a second cylindrical sheath 108 which surrounds a portion of the first sheath 121, and can be manipulated longitudinally along the first sheath to provide a means for modulating the exposure of the probe tip 22 and 23, and thereby modulating the cavitation energy emitted by the probe to which the tissues will be exposed. The container of the present invention is capable of receiving and containing the probe or probe and sheath assembly.
Figure 3A:
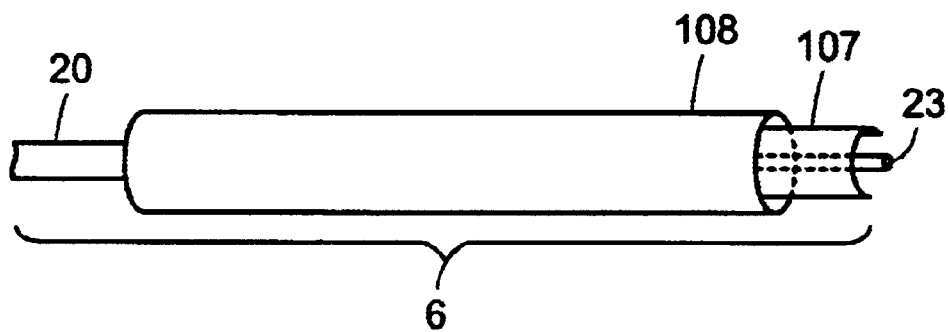
FIGS. 3a–f show dampening sheaths for an ultrasonic probe according to embodiments of the invention.
Figure 3B:
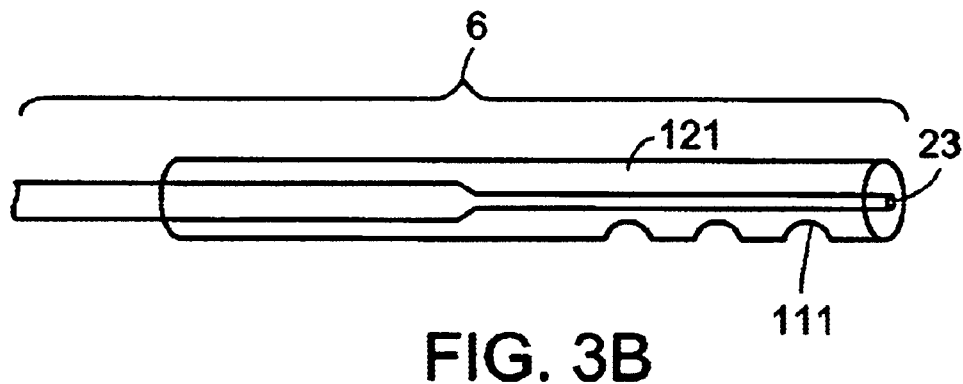
Figure 3C:
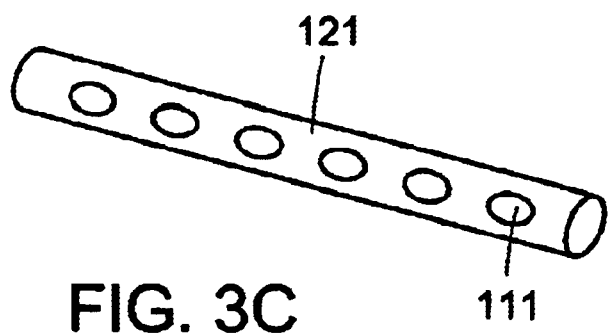
Figure 3D:
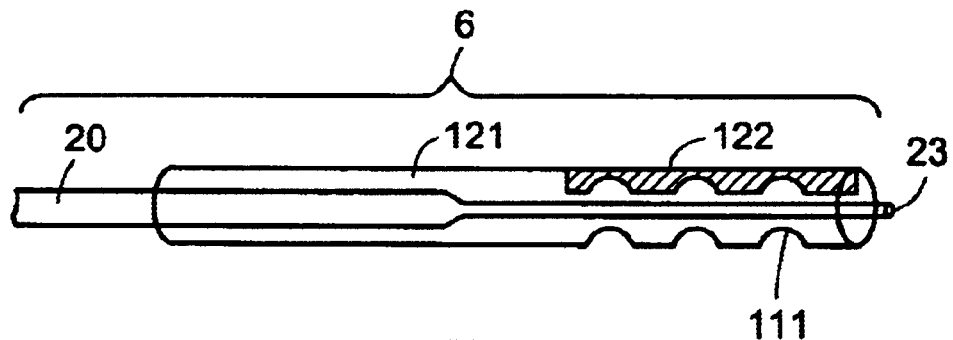
Figure 3E:
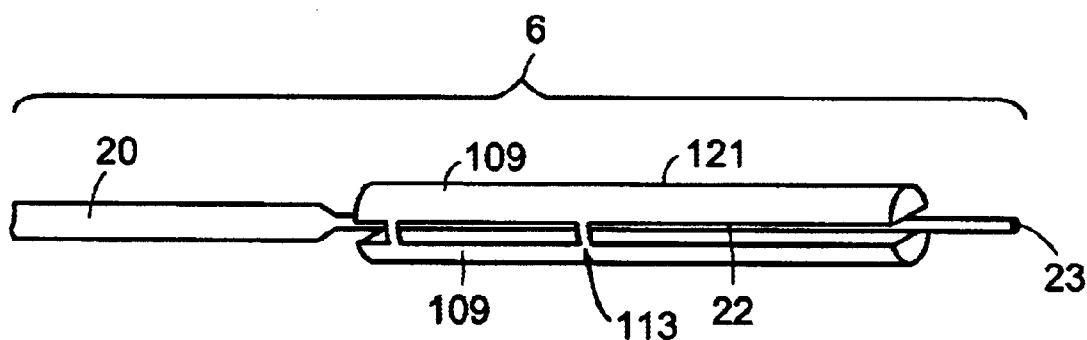
Figure 3F:
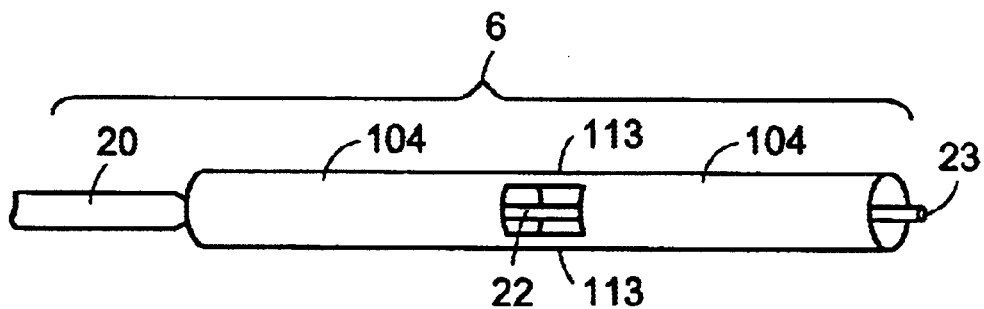
Figure 4:
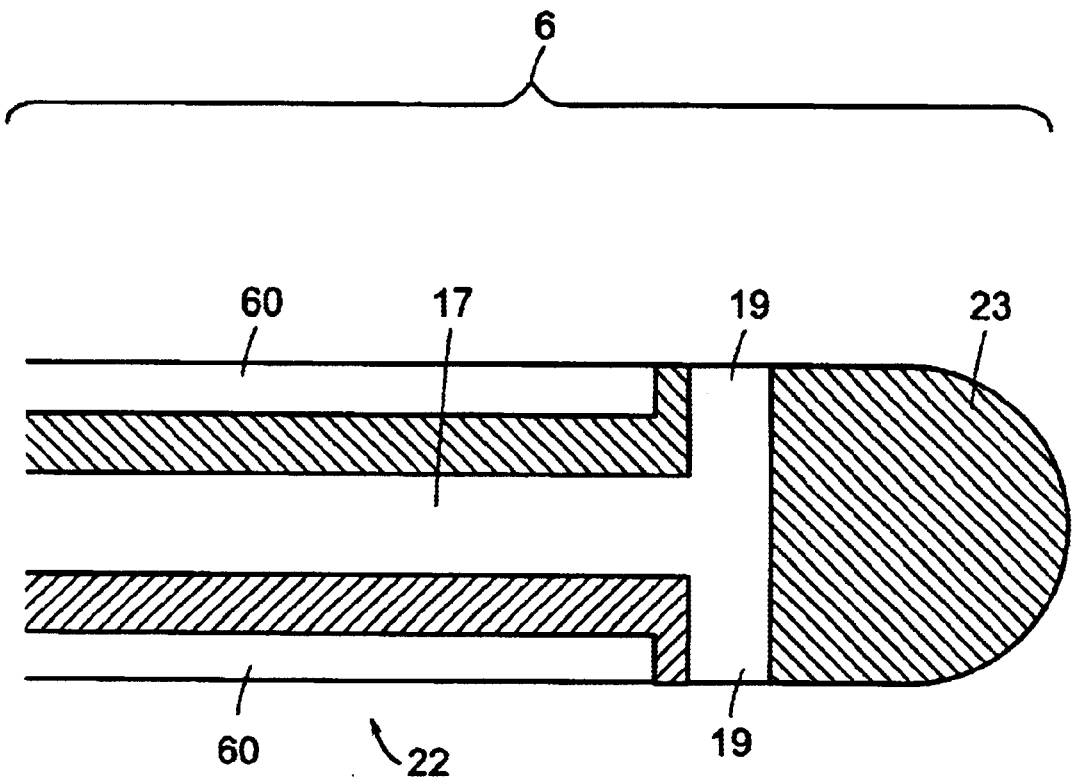
FIG. 4 shows a longitudinal cross-section of a portion of an ultrasonic probe tip 22 and 23 according to one embodiment of the invention, comprising a central irrigation passage 17 and lateral irrigation lumens 19, as well as external aspiration channels 60.

The following terms and definitions are used herein:

"Anti-node" as used herein refers to a region of minimum energy emitted by an ultrasonic probe on or proximal to a position along the probe.

"Cavitation" as used herein refers to shock waves produced by ultrasonic vibration, wherein the vibration creates a plurality of microscopic bubbles which rapidly collapse, resulting in molecular collision by water molecules which collide with force thereby producing the shock waves.

"Fenestration" as used herein refers to an aperture, window, opening, hole, or space.

"Node" as used herein refers to a region of maximum energy emitted by an ultrasonic probe on or proximal to a position along the probe.

"Probe" as used herein refers to a device capable of being adapted to an ultrasonic generator means, which is capable of propagating the energy emitted by the ultrasonic generator means along its length, and is capable of acoustic impedance transformation of ultrasound energy to mechanical energy.

"Sharps" as used herein refers to an elongated medical instrument with a small diameter, for example, less than 2 mm. A "Sharps Container" as used herein is a container capable of retaining a sharp medical device or the sharp portion thereof, such that a handler is not exposed to the sharp portion of the device.

"Sheath" as used herein refers to a device for covering, encasing, or shielding in whole or in part, a probe or portion thereof connected to an ultrasonic generation means.

"Tissue" as used herein refers to an aggregation of cells that is substantially similar in terms of morphology and functionality.

"Transverse" as used herein refers to vibration of a probe at right angles to the axis of a probe. A "transverse wave" as used herein is a wave propagated along an ultrasonic probe in which the direction of the disturbance at each point of the medium is perpendicular to the wave vector.

"Tuning" as used herein refers to a process of adjusting the frequency of the ultrasonic generator means to select a frequency that establishes a standing wave along the length of the probe.

"Ultrasonic" as used herein refers to a frequency range of the electromagnetic spectrum above the range of human hearing, i.e., greater than about 20,000 Hertz up to about 80,000 Hertz.

The present invention provides an ultrasonic medical device operating in a transverse mode for removing a vascular occlusion. Because the device is minimally invasive and articulable, it can be inserted into narrow, tortuous blood vessels without risking damage to those vessels. Transverse vibration of the probe in such a device generates multiple nodes of cavitation energy along the longitudinal axis of the probe, emanating radially from these nodes. The occlusion is fragmented to debris approximately of submicron sizes, and the transverse vibration generates a retrograde flow of debris that carries the debris away from the probe tip.

The mode of vibration of the ultrasound probe according to the invention differs from the axial mode of vibration which is conventional in the prior art. Rather than vibrating exclusively in the axial direction, the probe vibrates in a direction transverse to the axial direction. As a consequence of the transverse vibration of the probe, the tissue-destroying effects of the device are not limited to those regions of a tissue coming into contact with the tip of the probe. Rather, as the probe is positioned in proximity to an occlusion or other blockage of a blood vessel, the tissue is removed in all areas adjacent to the multiplicity of energetic nodes being produced along the entire length of the probe typically in a region having a radius of up to about 2 mm around the probe. In this way, actual treatment time using the transverse mode ultrasonic medical device according to the invention is greatly reduced as compared to methods using prior art probes.

The number of nodes occurring along the axial length of the probe is modulated by changing the frequency of energy supplied by the ultrasonic generator. The exact frequency, however, is not critical and a ultrasonic generator run at, for example, 20 kHz is generally sufficient to create an effective number of tissue destroying nodes along the axial length of the probe. In addition, as will be appreciated by those skilled in the art, it is possible to adjust the dimensions of the probe, including diameter, length, and distance to the ultrasonic energy generator, in order to affect the number and spacing of nodes along the probe. The present invention allows the use of ultrasonic energy to be applied to tissue selectively, because the probe conducts energy across a frequency range of from about 20 kHz through about 80 kHz. The amount of ultrasonic energy to be applied to a particular treatment site is a function of the amplitude and frequency of vibration of the probe. In general, the amplitude or throw rate of the energy is in the range of 150 microns to 250 microns, and the frequency in the range of 20–80 kHz. In the currently preferred embodiment, the frequency of ultrasonic energy is from 20,000 Hertz to 35,000 Hertz. Frequencies in this range are specifically destructive of hydrated (water-laden) tissues and vascular occlusive material, while substantially ineffective toward high-collagen connective tissue, or other fibrous tissues such as, for example, vascular tissues, or skin, or muscle tissues.

The amount of cavitation energy to be applied to a particular site requiring treatment is a function of the amplitude and frequency of vibration of the probe, as well as the longitudinal length of the probe tip, the proximity of the tip to a tissue, and the degree to which the probe tip is exposed to the tissues. Control over this last variable can be effectuated through the sheaths of the present invention.

Sheath materials useful for the present invention include any material with acoustical or vibrational dampening properties capable of absorbing, containing, or dissipating the cavitation energy emitted by the probe tip. Such materials must be capable of being sterilized by, for example, gamma irradiation or ethylene oxide gas (ETO), without losing their structural integrity. Such materials include but are not limited to, plastics such as polytetrafluoroethylene (PTFE), polyethylene, polypropylene, silicone, ultem, or other such plastics that can be used for medical procedures. Ceramic materials can also be used, and have the added benefit that they may be sterilized by autoclaving. Combinations of the aforementioned materials can be used depending on the procedure, for example as in the sheath of FIG. 5, a ceramic sheath 121 can be used in combination with a moveable PTFE outer sheath 108. Alternatively a single sheath may employ two or more materials to give the desired combination of strength and flexibility, for example, the sheath may comprise a rigid ceramic section distal to the probe tip 23 and a more flexible plastic section proximal to the tip, capable of flexing with the probe 22. In the currently preferred embodiment of the invention, PTFE is used to fabricate a strong, flexible, disposable sheath that is easily sterilized by irradiation or ETO gas.

The length and diameter of the sheath used in a particular operation will depend on the selection of the probe, the degree to which the probe length will be inserted into the subject, and the degree of shielding that is required. For example, in an application whereby vascular occlusive material is removed with the ultrasonic probe of the present invention, from a vessel deep inside the body of a patient, the sheath must be of a sufficient length to protect the vascular tissue from the surgical insertion point to the site of the operation, of a sufficient outside diameter to facilitate insertion of the sheath into the vessel, and a sufficient inside diameter capable of accepting the probe. By contrast, for clearing occlusions from, for example, a hemodialysis graft, the probe useful for such a procedure would be significantly shorter and as such, so would the sheath. The exact length and diameter of the sheath will be determined by the requirements of the medical procedure. Similarly, the position and size of the sheath aperture 111, or number and positions of the fenestrations 111, or the addition of a bevel on the sheath terminus 129, will likewise be determined by the type of procedure, and the requirements of the particular patient.

Figure 6A:
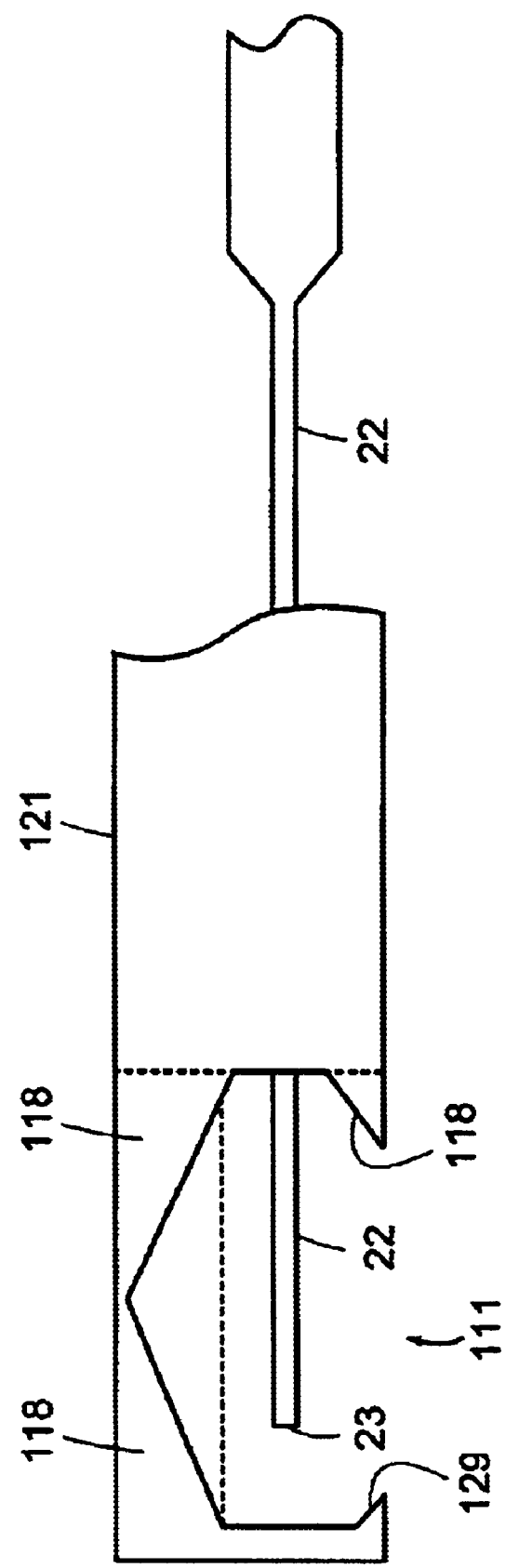
FIG. 6a shows an embodiment of the invention wherein the probe tip 22 and 23, is substantially contained within a sheath. The sheath comprises a fenestration 111 allowing communication of the cavitation energy emitted by the probe to the outside of the sheath. The interior of the sheath further comprises reflective elements 118, shown as a plurality of planar surfaces that extend from the interior wall of the sheath into the lumen, thereby providing a means for focussing and redirecting cavitation energy emitted by the probe tip. In this embodiment, the terminus of the sheath 129 is shaped to provide a tissue manipulation means also illustrated in FIG. 5.
Figure 6B:
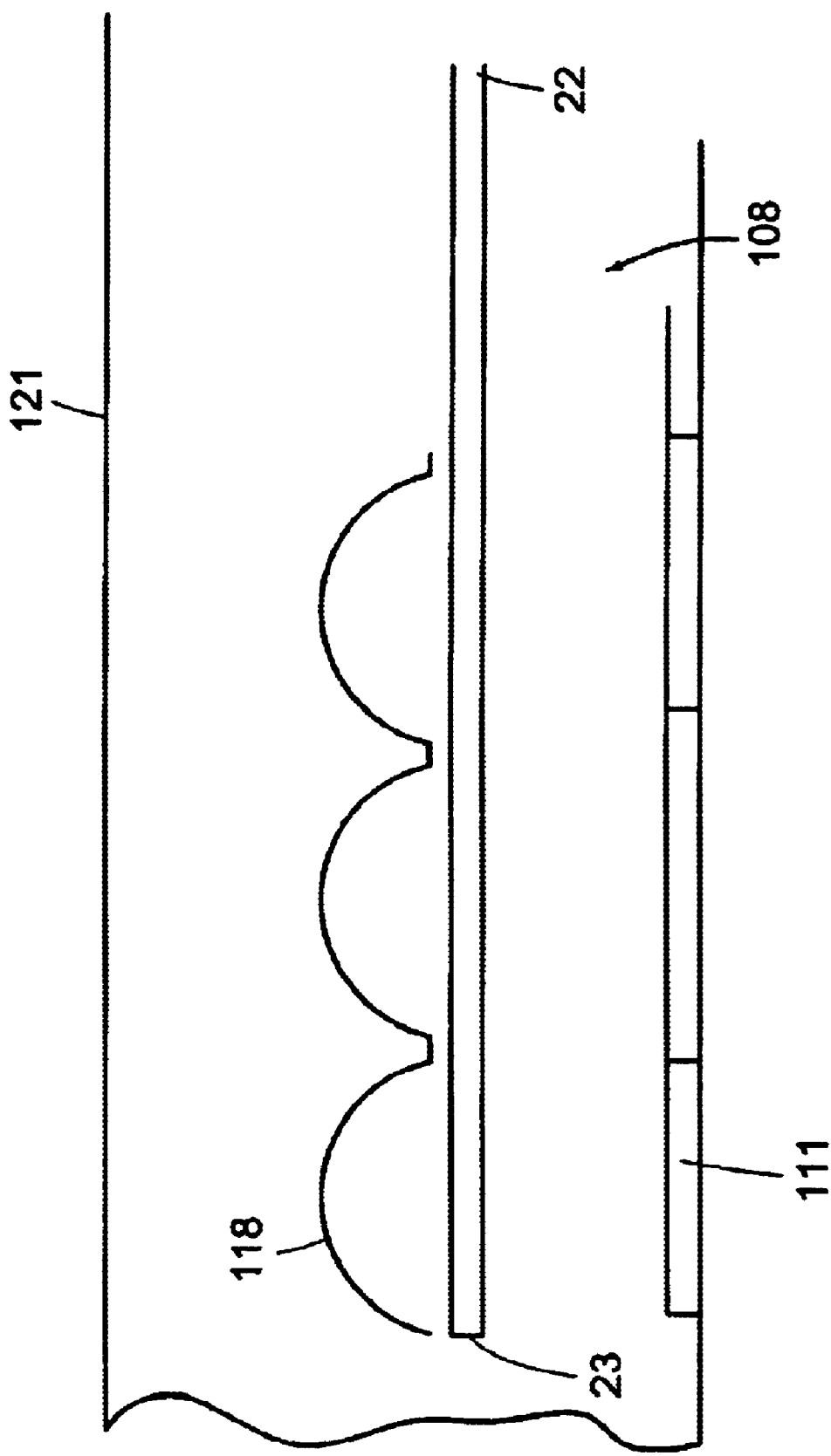
FIG. 6b shows a similar embodiment, wherein the reflective elements 118 are arcutate, and the sheath further comprises a plurality of fenestrations 111.
Figure 7A:
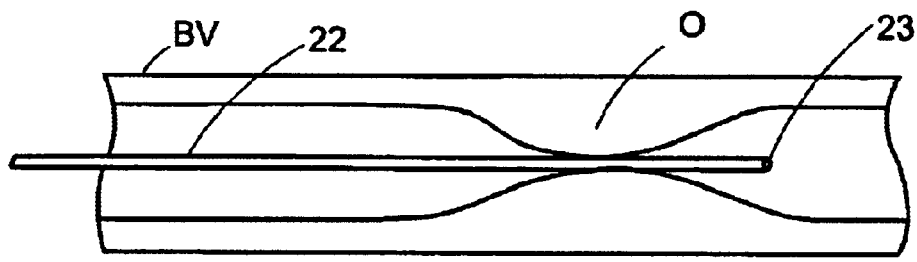
FIG. 7a shows a portion of the probe 22 guided to the site of, and through the occlusion, using ultrasonic energy to fragment occlusion materials and clear a path through the occlusion.
Figure 7B:
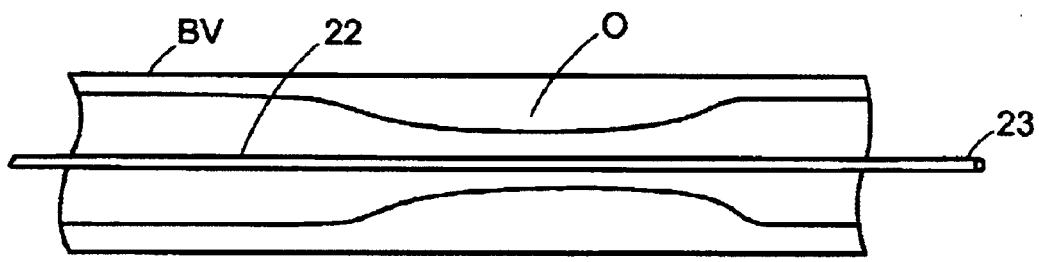
FIG. 7b shows the occlusion within the blood vessel partially removed by action of the probe.
Figure 7C:
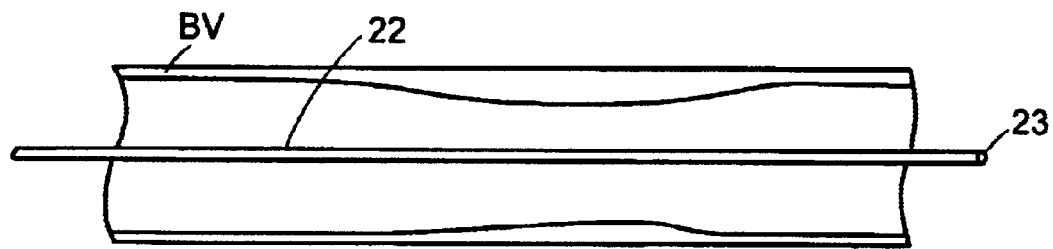
FIG. 7c shows complete removal of the occlusion as occlusion materials are degraded by the energy transmitted by the probe 22 of the ultrasonic medical device.

A particular advantage of the ultrasonic probe operating in transverse mode is that the efficient cavitation energy produced by the probe disintegrates target tissue to small particles of approximately sub-micron diameter. Because of the operation of the probe, tissue debris created at the probe tip 23, is propelled in a retrograde direction from the probe tip. Accordingly, another embodiment of the invention, provides at least one aspiration channel which can be adapted to a vacuum or suction device, to remove the tissue debris created by the action of the probe. The aspiration channel can be manufactured out of the same material as the sheath provided it is of a sufficient rigidity to maintain its structural integrity under the negative pressure produced by the aspiration means. Such an aspiration channel could be provided inside the lumen of the sheath, or along the exterior surface of the sheath, or the sheath itself may provide the aspiration channel. One embodiment of this is shown in FIGS. 6 and 7, whereby the probe 22 comprises at least one aspiration channel 60, and aspiration of tissue debris is effectuated along the probe length between the interior surface of the sheath and the exterior surface of the probe, as directed by the aspiration channels.

In another embodiment, the present invention comprises an irrigation channel. The sheath is adapted to an irrigation means, and the sheath directs fluid to the location of the probe 22. The irrigation channel can be manufactured out of the same material as the sheath provided it is of a sufficient rigidity to maintain its structural integrity under the positive pressure produced by the flow of fluid produced by the irrigation means. Such an irrigation channel could be provided inside the lumen of the sheath, or along the exterior surface of the sheath, or the sheath itself may provide the aspiration channel. Using the sheath itself to provide the irrigation, there is an added benefit that the probe 22 is cooled by the fluid.

In yet another embodiment, the sheath of the present invention further comprises both an irrigation and an aspiration channel. As in the above embodiments, the channels may be located within the sheath lumen, or exterior to the sheath, or a combination of the two. Likewise, the sheath lumen itself may provide either an irrigation or aspiration channel, with the corresponding irrigation or aspiration channel either contained within or external to the sheath. In another aspect of the invention, the sheath comprises a means for directing, controlling, regulating, and focussing the cavitation energy emitted by the probe, an aspiration means, an irrigation means, or any combination of the above.

Another embodiment of the invention comprises a means of viewing the site of probe action. This may include an illumination means and a viewing means. In one embodiment, the sheath of the present invention comprises a means for containing or introducing (if external to the sheath) an endoscope, or similar optical imaging means. In another embodiment of the invention, the ultrasound medical device is used in conjunction with an imaging system, for example, the non-ferrous probes are compatible with MRI, or ultrasound imaging—in particular color ultrasound. In this embodiment, the action of the probe echogenically produces a pronounced and bright image on the display. The sheath in this embodiment shields the probe, thereby reducing the intensity of the probe image and enhancing the resolution of the surrounding tissues. In another embodiment of the invention (not shown), the probe is used with an optical system. In one embodiment, the probe is inserted into a body cavity or lumen along with a light transmitting element for transmitting light from a light source and for receiving light and transmitting received light to a detector. Light from a light source (e.g., a laser) is transmitted through the light transmitting element, illuminating the area surrounding the probe 6, and light transmitted back through the light transmitting element (e.g., from tissue in the vicinity of the probe) is detected by the detector. In one embodiment of the invention, the light transmitting element is an optical fiber, while in another embodiment, the light transmitting element is a plurality of optical fibers. The light transmitting element can be a part of the probe or can be inserted into a body cavity independently of the probe. In one embodiment of the invention, a sleeve is attached to the probe and the light transmitting element is held within the sleeve. In one embodiment, the detector is a human being (e.g., a physician or lab technician) and light is monitored using a viewing element, such as an eyepiece (e.g., as in a microscope coupled to the light transmitting element). It is preferred that the viewing element is not connected to a part of the ultrasonic medical device which is subject to vibration, to reduce manipulation of the viewing system to a minimum. In another embodiment of the invention, the detector is in communication with a processor and converts optical signals from the light transmitting element to data relating to the tissue in the vicinity of the probe.

Figure 8A:
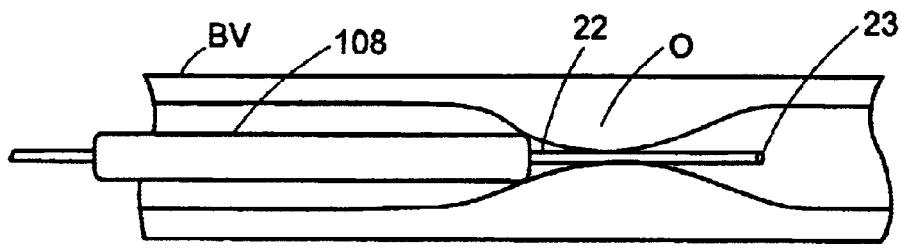
FIG. 8a shows a sheath assembly consisting of a sheath 108 adapted to a portion of the probe 22. The probe is positioned proximally to the site of, and through the occlusion, using ultrasonic energy to fragment occlusion materials and clear a path through the occlusion, while the sheath protects non-occluded areas of the blood vessel by partially shielding the probe.
Figure 8B:
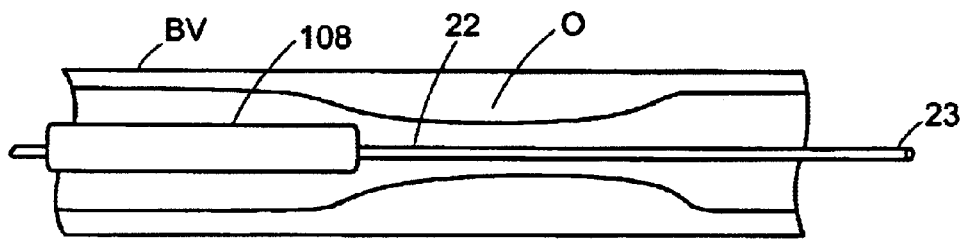
FIG. 8b shows the occlusion within the blood vessel partially removed by action of the probe, while the sheath is retracted to maintain exposure of the probe at occlusion site as it is moved through the site.
Figure 8C:
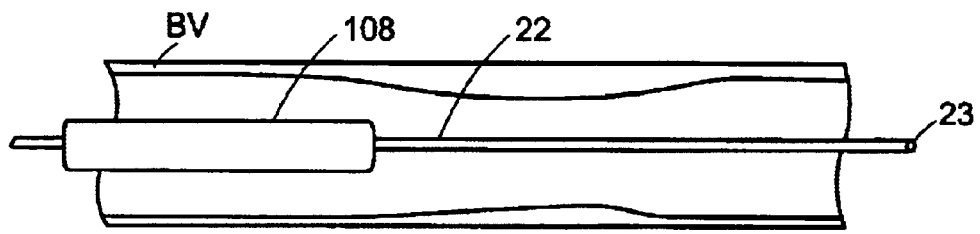
FIG. 8c shows complete removal of the occlusion, as occlusion materials are degraded by the energy transmitted by the probe 22 of the device, while non-occluded areas of the blood vessel remain protected from the action of the probe.
Figure 9A:
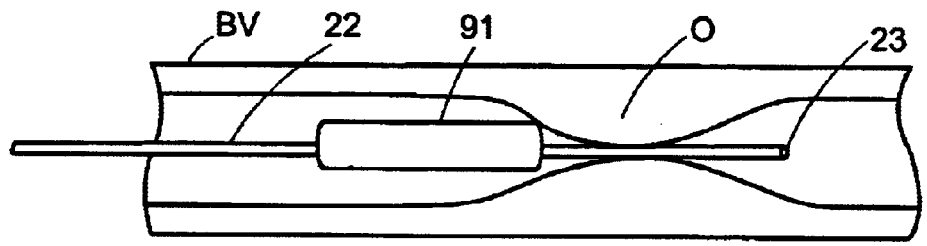
FIG. 9a shows the deflated balloon catheter 91 adapted to a portion of a probe 22. The probe guides the catheter to the site of, and through the occlusion, using ultrasonic energy to clear a path through the occlusion if necessary.
Figure 9B:
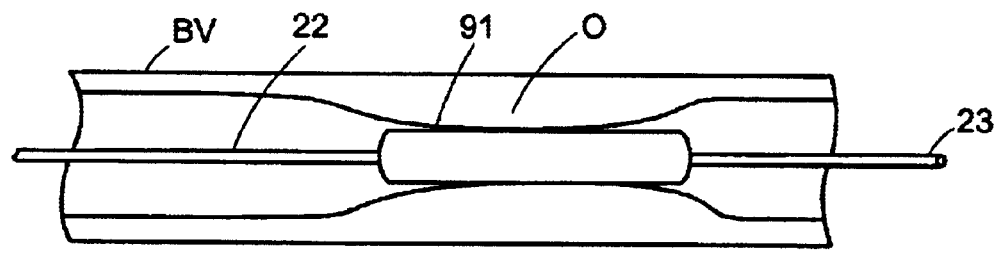
FIG. 9b shows the deflated balloon catheter 91 positioned within the vessel lumen at the site of the occlusion.
Figure 9C:
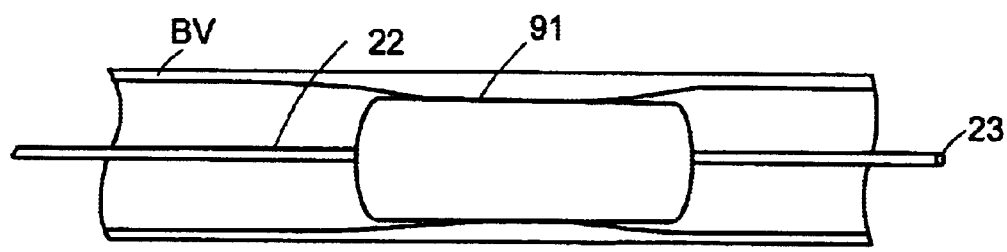
FIG. 9c shows an activated ultrasonic medical device wherein the expanded balloon catheter engages the occlusion, maintaining contact with the occlusion as it is degraded by the energy transmitted through the balloon.

In one embodiment, as shown in FIG. 8, the sheath comprises a surface that is capable of manipulating tissues near the site of the probe. In this aspect, the terminus of the sheath may be closed, such that the sheath insulates tissues from the destructive energy emitted by the probe and can be used to push tissues away from the aperture 111, thereby allowing proximal tissues to be exposed to the probe 22 and 23. Alternatively, the sheath comprises a beveled or arcutate surface at the sheath terminus 129, capable of providing a means for hooking, grasping, or otherwise holding a tissue in proximity to the probe 22 and 23. In another embodiment, the sheath provides a means for introducing a surgical device, for example, flexible biopsy forceps, capable of manipulating tissues into a tissue space, such that the surgical device can hold the tissue in proximity with the probe.

Figure 5:
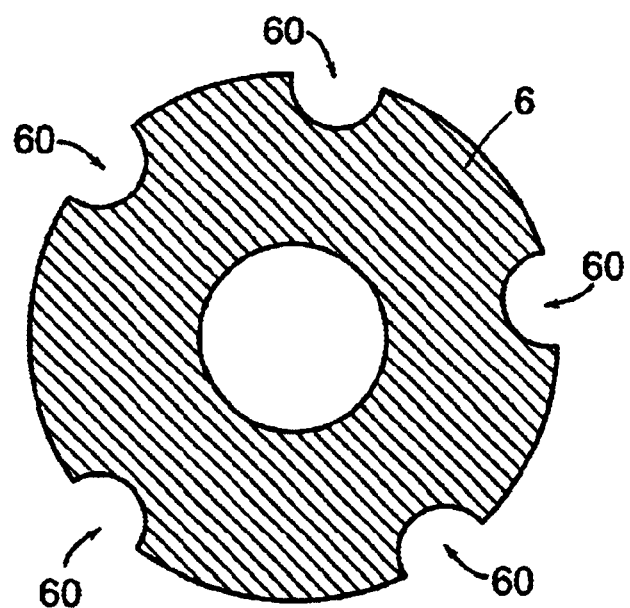
FIG. 5 shows a transverse cross-section of a portion of the ultrasonic probe shown in FIG. 4. In this embodiment, the probe 6 comprises a plurality of arcutate channels 60 that extend over the longitudinal length of the probe tip, providing a space for irrigation and or aspiration of tissue debris and fluid.
Figure 10A:
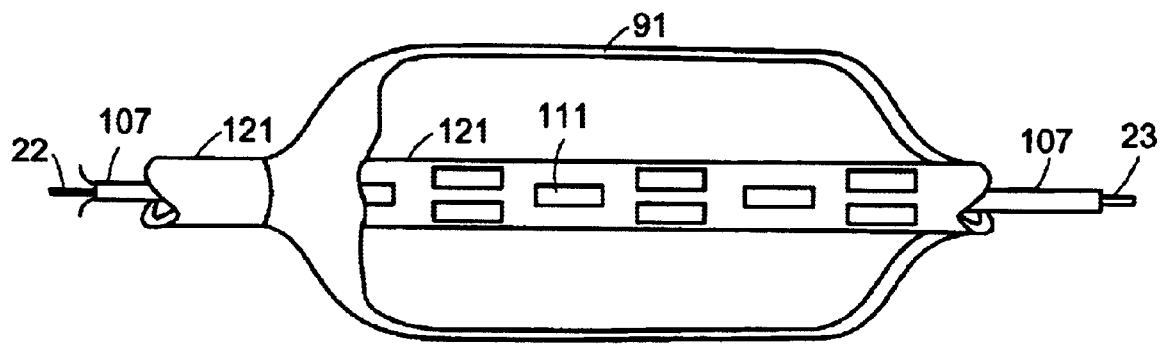
In FIG. 10a, the invention of the present embodiment comprises a probe 22 with a terminal end 23, substantially contained within a first sheath 107 of which the end distal to the probe tip 23, is shown cut away for illustrative purposes. The balloon catheter is adapted to an inflation means (not shown), which may also comprise a means for monitoring and compensating for pressure fluctuation in the interior of the balloon. The probe and first sheath is substantially contained within a second sheath 121, further comprising a series of fenestrations 111 along its longitude. The balloon catheter 91, shown substantially deflated, surrounds the second sheath along part of its length. In this embodiment, the probe tip 23 is exposed to the vessel lumen and can provide a means for clearing a path through an occlusion for the introduction of a balloon catheter.
Figure 10B:
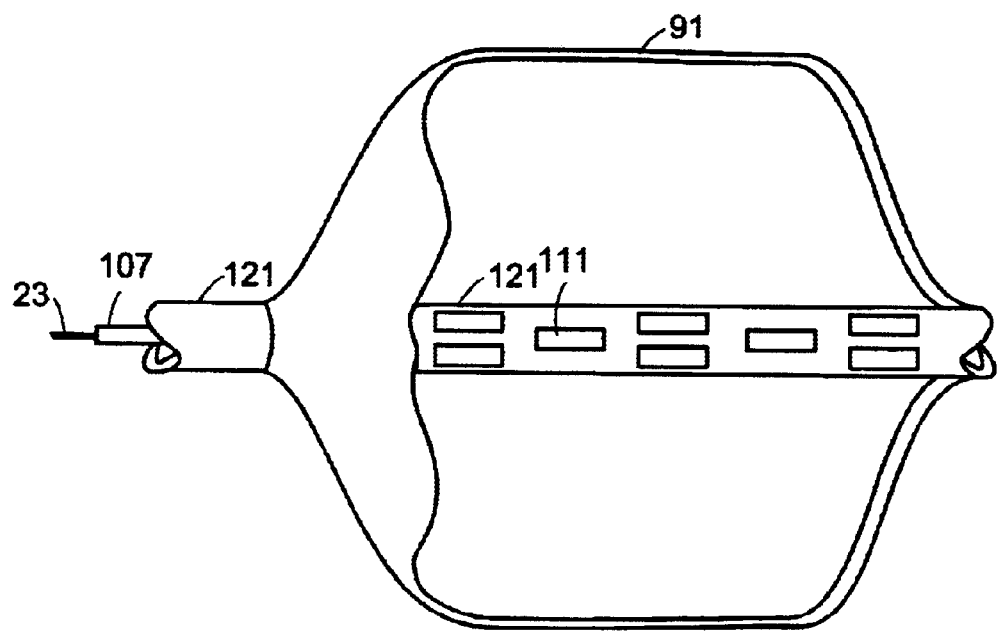
In FIG. 10b, the probe 22 and 23 is withdrawn such that the tip 23, is contained within the sheath 121. The first sheath 107 is retracted, by for example, articulation wires, thereby exposing the probe 22 to the lumen of the second sheath 121. Activation of the probe results in the transverse generation of cavitation energy along the probe at multiple nodes. The energy is communicated from the probe to the lumen of the balloon catheter through the fenestrations 111 in the second sheath 121. The energy can penetrate the walls of the balloon for direct communication to the occlusion.

In one aspect of the invention, as shown in FIG. 5, the sheath comprises an inner sheath 121 and an outer sheath 108. The outer sheath may be connected to an retraction trigger (not shown), by one or more articulation means, such as wires, which is capable of moving the outer sheath with respect to the inner sheath. Each wire comprises a first end and a second end. The first end is affixed to the outer sheath 108, while the second end is affixed to a retraction trigger. When the outer sheath 108 is slid back away from the terminus of the inner sheath 121 the tissues are exposed to cavitation energy emitted by the probe. Another aspect of this is referred to in FIG. 10, where the first sheath 107, is adapted to articulation wires (not shown in the illustration). In this embodiment, moving the sheath exposes the probe to the lumen of a second sheath 121, comprising fenestrations which allow communication of the energy emitted from the probe to the lumen of a balloon catheter 91. In this aspect, a probe can be operational without inflating the balloon catheter until movement of the first sheath exposes the probe, thereby allowing the probe to penetrate occlusions that would otherwise prevent placement of the balloon catheter without first clearing a site for placement within the occlusion, and thereby reducing the number of steps in a surgical procedure.

In another embodiment, the probe and sheath are flexible. Articulation wires (not shown) comprising a first end and a second end, are connected to the sheath and to an articulation handle. When the articulation handle is manipulated, for example, pulled axially inward, the flexible sheath will bend or articulate in a bending or articulation direction A, thereby causing the ultrasonic probe to bend or articulate in articulation direction A. In this way, the ultrasonic probe can be used to reach locations which are not axially aligned with the lumen or vessel through which the sheath and probe are inserted. One aspect of the invention uses such an articulable sheath to direct placement of a probe and a balloon catheter to a surgical site.

In yet another embodiment, the sheaths of the present invention may be provided along with an ultrasonic probe in the form of a kit. In this aspect, the probe for a particular surgical procedure is provided along with the correct sheath, as well as instructions for assembling and tuning the probe, and the appropriate frequency range for the procedure. The probe and sheath may be packaged preassembled, such that the probe is already contained within the sheath and the respective position of the probe within the sheath is optimized such that any reflective elements in the sheath would be correctly aligned with the prospective position of the nodes for a given frequency, the kit further comprising instructions for the appropriate frequency. The kit may further comprise packaging whereby the probe and sheath are pre-sterilized, and sealed against contaminants. In another embodiment, the probe and sheath is provided in a container that complies with regulations governing the storage, handling, and disposal of sharp medical devices. Such a container is capable of receiving and securing the probe and sheath before and after use. In one aspect, the sharps container provides a means of affixing the probe and sheath assembly to an ultrasonic medical device without direct manipulation of the probe and sheath assembly, and a means for removing the assembly from the ultrasonic medical device after use. In one aspect, the kit comprises a probe and sheath assembly contained within a sterile sharps container that further comprises a single use locking means, whereby the probe and sheath assembly is affixed to the ultrasonic medical device solely through the sharps container, are removed from the device solely through the container, and once removed can not be re-extracted from the sharps container.

EXAMPLES

Example 1

Removing Occlusions Using An Ultrasonic Medical Device and a Balloon Catheter

In one embodiment of the invention, the transverse mode ultrasonic medical device, is used in a procedure to remove an occlusion from a small diameter vessel (e.g., a native vessel, or a grafted vessel). In one embodiment, device is used in a method to reduce or eliminate an occlusion of a saphenous vein graft (e.g., such as used in a coronary bypass procedure).

A transverse mode ultrasonic probe is selected by the surgeon who will perform the procedure. The probe of the present invention further comprises a plurality of sheaths adapted to the probe, and a balloon catheter operably attached to one of the sheaths, all incorporated within a sharps container, and the container further sealed inside a sterile package, for example, a plastic bag. The user removes the container from the package and attaches the probe to the ultrasonic medical device by applying the threaded end of the probe to the transducer portion of an ultrasonic medical device. The probe, sheaths, and balloon catheter are securely held within the container, and the user rotates the container to affix the probe, sheaths, and catheter to the ultrasonic medical device. The user engages a lever which articulates the side A first locking assembly, thereby disengaging the probe from the first locking assembly. The probe, sheaths, and catheter can now be withdrawn from the container. The first locking assembly, once articulated, is engaged and held stationary by a second locking means, thereby preventing further use of the first locking assembly on this side A of the container with a probe. Articulation wires attached to one of the sheaths, are connected to a trigger assembly so the first sheath can be moved relative to the second sheath and the probe. One terminus of the balloon catheter is connected to an inflation means that may further comprise a means of monitoring and adjusting for pressure changes in the balloon lumen.

A small incision is made into the chest of a patient, and the vein graft is visualized using routine imaging technology. The probe, sheaths, and balloon catheter assembly is introduced into a vessel near the site of the occlusion, by way of, for example, a trocar or other vascular introducer. The probe assembly is guided to the site of the occlusion. The probe may be operably emitting energy, but the position of the first sheath relative to the probe and second sheath prevents cavitation energy from the probe from entering the balloon catheter, and the exposed probe terminus allows for introduction of the assembly, specifically the balloon catheter into the interior of the occlusion, as the occlusion is fragmented around the probe. The balloon catheter is inflated to greater than ambient pressure, such as for example, 1.5 atmospheres, so that the balloon is in contact with the occlusion but does not exert a high degree of compressive force on the occlusion or the vessel wall. The transversely vibrating probe is exposed to the lumen of the balloon by articulation of the first sheath. Cavitation energy from the probe is transmitted to the occlusion through the polymer walls of the balloon, thereby fragmenting the occlusion. As the occlusion is destroyed, allowing expansion of the balloon, the pressure drop is sensed and compensated for, by the inflation means, thereby the balloon re-engages the surface of the occlusion. The process continues for an appropriate length of time determined by the surgeon. When the procedure is completed, the balloon catheter is deflated, and the catheter, sheaths, and probe are withdrawn from the patient. The insertion device is removed, and the vascular tear, and surgical incision are sutured.

When the user completes the surgical procedure, and the probe apparatus is no longer required, the user inserts the probe, sheaths, and balloon catheter into side B of the container. The user engages a lever which articulates the side B first locking assembly, which, once articulated, is engaged and held stationary by a second locking means, thereby preventing further articulation of the side B first locking assembly. This first locking assembly engages the probe, thereby securing it. The user removes the probe assembly from the transducer of the medical device by applying counter-rotational torque to the container, thereby unscrewing the probe from the device. The used probe and assembly is permanently engaged by and contained within the container, and can be disposed of in compliance with the provisions governing the disposal of medical waste. Because the probe assembly is contained by the invention, the sharp probe tip does not present a safety hazard, and can be safely handled and disposed of as medical trash.

Example 2
Clearing Occlusions from a Hemodialysis Graft

In another embodiment, the invention can be used to clear occlusions from and restore the patency of a hemodialysis graft. The graft will not require shielding from ultrasonic energy, or the use of a balloon catheter as in example 1. A probe is selected and affixed to the ultrasonic transducer in the manner previously described, through the use of the container. The probe is withdrawn from the container, and inserted into the lumen of the hemodialysis graft. In one embodiment, the probe is directly introduced into the hemodialysis graft. In another embodiment, the probe is inserted using a trocar or other vascular insertion device, such as for example, the insertion device of Applicant's utility application Ser. No. 09/618,352. Application of ultrasonic energy causes the probe to vibrate transversely along its longitude. Occlusive materials, such as for example a thrombus, are fragmented by the action of the probe. When the graft has been returned to patency, the probe is withdrawn. The probe is removed from the device with the sharps container.

Variations, modifications, and other implementations of what is described herein will occur to those of ordinary skill in the art without departing from the spirit and scope of the invention as claimed. Accordingly, the invention is to be defined not by the preceding illustrative description but instead by the spirit and scope of the following claims. The following references provided include additional information, the entirety of which is incorporated herein by reference.

We claim:

1. An ultrasonic medical device for removing vascular occlusions comprising: a transducer capable of vibrating at an ultrasonic frequency, a probe engaging said transducer, said probe capable of translating the vibrations from said transducer and thereby vibrating transversely along its longitude thus creating a plurality of nodes of cavitation energy along at least a portion of a longitudinal axis of said probe, wherein said plurality of nodes of cavitation energy create an occlusion destroying effect along at least a portion of said longitudinal axis of said probe.

2. The ultrasonic medical device of claim 1 whereby said transverse vibration along said longitudinal axis of said probe further causes a node of cavitation energy at the distal end of said probe.

3. The ultrasonic medical device of claim 2 wherein the cavitation energy produced at the distal end of said probe is capable of fragmenting vascular occlusive material to submicron sized particles and is capable of effectuating retrograde flow of said fragmented vascular occlusive material away from the distal end of said probe.

4. The ultrasonic medical device of claim 2 further comprising a sheath engaging said probe.

5. The ultrasonic medical device of claim 4 wherein said sheath further comprises an aspiration means.

6. The ultrasonic medical device of claim 4 or claim 5 wherein said sheath further comprises an imaging means.

7. An ultrasonic medical device for removing vascular occlusions comprising: a transducer capable of vibrating at an ultrasonic frequency, a probe engaging said transducer, said probe capable of translating the vibrations from said transducer and thereby vibrating transversely along at least a portion of a longitudinal axis thus creating a plurality of nodes of cavitation energy along at least a portion of said longitudinal axis of said probe wherein said plurality of nodes of cavitation energy create an occlusion destroying effect along at least a portion of said longitudinal axis of said probe, and a balloon catheter engaging a portion of said probe, said balloon catheter capable of being adapted to an inflation means and a deflation means.

8. The ultrasonic medical device of claim 7 further comprising a sheath engaging said probe.

9. The ultrasonic medical device of claim 8 wherein said sheath further comprises an aspiration means.

10. The ultrasonic medical device of claim 7 or claim 8 wherein said sheath further comprises an imaging means.

11. A kit for removing an occlusion in a vessel comprising: a probe capable of vibrating transversely along a longitudinal axis thus creating a plurality of nodes of cavitation energy along at least a portion of said longitudinal axis of said probe wherein said plurality of nodes of cavitation energy create an occlusion destroying effect along at least a portion of said longitudinal axis of said probe; and an appropriate packaging to contain and maintain the sterility of the contents of the kit.

12. The kit of claim 11 further comprising a sheath engaging said probe.

13. The kit of claim 11 or claim 12 further comprising a balloon catheter engaging a portion of said probe, said balloon catheter capable of being adapted to an inflation means and a deflation means.

14. A method of removing an occlusion from a vessel with an ultrasonic medical device capable of transverse vibration along at least a portion of a longitudinal axis of the probe of said device, comprising the steps of:
   a) inserting a probe of an ultrasonic medical device into said vessel;
   b) positioning said probe in proximity to said occlusion;
   c) providing ultrasonic energy to said medical device thereby causing transverse vibration of said probe and the generation of a plurality of nodes of cavitation energy along at least a portion of said longitudinal axis of said probe wherein said plurality of nodes of cavitation energy create an occlusion destroying effect along at least a portion of said longitudinal axis of said probe; and
   d) fragmenting said occlusion through the cavitation energy emitted by said probe.

15. The method of claim 14 wherein the probe is at least partially contained within a sheath further comprising at least one fenestration, said probe and sheath positioned such that said fenestration is in proximity with the occlusion.

16. The method of claim 15 wherein the sheath further comprises an aspiration means, and fragment of said occlusion generated from cavitation at the distal end of the probe are directed, in a retrograde direction from the distal end of said probe, said fragments remove through said aspiration means.

17. The method of claim 14 or claim 15 wherein the sheath further comprises an imaging means enabling the positioning of said probe proximal to said occlusion.

18. The method of claim 14 wherein the probe further comprises a balloon catheter engaging a portion of said probe, said balloon catheter capable of engaging an inflation means and a deflation means, and further comprising the steps of inserting the probe and balloon catheter into a vessel, positioning the balloon catheter proximal to the occlusion, inflating the balloon catheter so the balloon catheter contacts the surface of the occlusion, applying ultrasonic energy to said probe to fragment the occlusion, further inflating said balloon catheter to maintain contact with the occlusion while the occlusion is fragmented, deflating the balloon, and withdrawing the probe and balloon from the vessel.

19. An ultrasonic medical device for removing an occlusion in a blood vessel comprising:
   an elongated, flexible probe having a first terminus, a second terminus and a longitudinal axis therebetween; and
   a transducer coupled to said elongated, flexible probe at said first terminus wherein said transducer is capable of vibrating at an ultrasonic frequency to enable a translation of an acoustical energy from said transducer to said elongated, flexible probe, causing a transverse vibration along at least a portion of said longitudinal axis of said elongated, flexible probe creating an occlusion destroying effect along at least a portion of said longitudinal axis of said elongated, flexible probe.

20. The ultrasonic device of claim 19 further comprising a sheath assembly adapted to said elongated, flexible probe consisting of an at least one sheath.

21. The ultrasonic medical device of claim 20 wherein said sheath assembly further comprises an at least one irrigation channel.

22. The ultrasonic medical device of claim 20 wherein said sheath assembly further comprises an at least one aspiration channel.

23. The ultrasonic medical device of claim 20 wherein said sheath assembly further comprises an at least one channel for delivering a drug therethrough.

24. The ultrasonic medical device of claim 20 wherein said sheath assembly further comprises an imaging device.

25. The ultrasonic medical device of claim 20 wherein a flexibility of said elongated, flexible probe.

26. The ultrasonic medical device of claim 19 further comprising a balloon catheter engaging at least a portion of said elongated, flexible probe, said balloon catheter capable of being engaged to an inflation apparatus and a deflation apparatus.

27. The ultrasonic medical device of claim 26 further comprising a sheath assembly engaged to said elongated, flexible probe consisting of an at least one sheath.

28. The ultrasonic medical device of claim 19 wherein said transverse vibrations along at least a portion of said longitudinal axis of said elongated, flexible probe creates a plurality of nodes of cavitation-energy along at least a portion of said longitudinal axis of said elongated, flexible probe.

29. The ultrasonic medical device according to claim 28 wherein said nodes of cavitation energy are capable of disrupting an occlusive materials within said blood vessel and causing fragmentation of said materials.

30. The ultrasonic medical device according to claim 28 wherein said nodes of cavitation energy is capable of effectuating retrograde flow of said fragmented occlusive materials away from said second terminus of said elongated, flexible probe.

31. An ultrasonic medical device comprising:
   an elongated flexible probe with a plurality of intervals each having a varying diameter along a longitudinal axis of the elongated, flexible probe;
   a first terminus of the longitudinal axis having a largest diameter of the elongated, flexible probe; and
   a second terminus of the longitudinal axis having a smallest diameter of the elongated, flexible probe;
   wherein the elongated, flexible probe can support a transverse ultrasonic vibration along at least a portion of the longitudinal axis that causes an occlusion destroying effect along at least a portion of the longitudinal axis of the elongated, flexible probe.

32. The ultrasonic medical device of claim 31 wherein the elongated, flexible probe is disposable.

33. The ultrasonic medical device of claim 31 wherein a diameter transition is located between each of the plurality of intervals along the longitudinal axis of the elongated, flexible probe.

34. The ultrasonic medical device of claim 31 wherein the diameter of the elongated, flexible probe decreases in gradual steps at the intervals from the first terminus to the second terminus of the elongated, flexible probe.

35. The ultrasonic medical device of claim 31 wherein the diameter of the elongated, flexible probe decreases from the first terminus of the longitudinal axis of the elongated, flexible probe to the second terminus of the longitudinal axis of the elongated, flexible probe.

36. The ultrasonic medical device of claim 31 further comprising a disposable sheath.

37. The ultrasonic medical device of claim 31 wherein a flexibility of the elongated probe allows the probe to be articulated.

* * * * *